(12) United States Patent
Carson

(10) Patent No.: US 7,662,156 B2
(45) Date of Patent: Feb. 16, 2010

(54) SYSTEMS AND PROCESSES FOR DETERMINING PROPER SUPERIOR-INFERIOR JOINT LINE POSITIONING

(75) Inventor: Christopher P. Carson, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 292 days.

(21) Appl. No.: 10/873,041

(22) Filed: Jun. 22, 2004

(65) Prior Publication Data

US 2005/0283249 A1 Dec. 22, 2005

(51) Int. Cl.
*A61F 2/76* (2006.01)
(52) U.S. Cl. .................... 606/102; 606/88; 623/914
(58) Field of Classification Search .............. 606/102, 606/88
See application file for complete search history.

(56) References Cited

U.S. PATENT DOCUMENTS

| 4,524,766 A | | 6/1985 | Petersen |
| 4,935,023 A | * | 6/1990 | Whiteside et al. ............ 606/88 |
| 5,226,915 A | * | 7/1993 | Bertin ..................... 623/20.15 |
| 5,306,276 A | | 4/1994 | Johnson et al. |
| 5,326,363 A | | 7/1994 | Aikins |
| 5,423,828 A | | 6/1995 | Benson |
| 5,464,406 A | * | 11/1995 | Ritter et al. ................ 606/86 |
| 5,470,354 A | | 11/1995 | Hershberger et al. |
| 5,540,696 A | * | 7/1996 | Booth, Jr. et al. ............ 606/88 |
| 5,571,197 A | * | 11/1996 | Insall ..................... 623/20.21 |
| 5,681,316 A | | 10/1997 | DeOrio et al. |
| 5,776,201 A | * | 7/1998 | Colleran et al. .......... 623/20.15 |
| 6,080,196 A | | 6/2000 | Bertin |
| 2002/0082607 A1 | * | 6/2002 | Heldreth et al. ............ 606/102 |
| 2006/0015120 A1 | | 1/2006 | Richard et al. |

OTHER PUBLICATIONS

Grelsamer, R. P., 'Patella Baja After Total Knee Arthroplasty,' *J. Arthro.*, 17(1):66-69 (2002).

* cited by examiner

*Primary Examiner*—Eduardo C Robert
*Assistant Examiner*—Jerry Cumberledge
(74) *Attorney, Agent, or Firm*—Kilpatrick Stockton LLP

(57) ABSTRACT

According to one embodiment, a method for determining a joint line position includes: providing a femoral trial component, the femoral trial component comprising an anterior flange and at least one mark on the anterior flange of the femoral trial component to indicate a desired patellofemoral contact point in extension; referencing the mark on the femoral trial component during a surgical procedure to assist in determining a proper superior-inferior joint line position between a tibial prosthetic component and a femoral prosthetic component; installing the femoral prosthetic component based at least in part on the determination of the proper superior-inferior joint line position between the tibial component and the femoral component; installing the tibial prosthetic component based at least in part on the determination of the proper superior-inferior joint line position; and completing the surgical procedure with the femoral component and tibial component in proper position is described.

12 Claims, 3 Drawing Sheets

SYSTEMS AND PROCESSES FOR DETERMINING PROPER SUPERIOR-INFERIOR JOINT LINE POSITIONING

FIELD OF THE INVENTION

The invention relates generally to systems, methods, and apparatuses related to prosthetic or orthopedic implants, and more specifically to systems, methods, and apparatuses for determining proper superior-inferior joint line positioning.

BACKGROUND

In a total knee arthroplasty, portions of the distal femur, and proximal tibia are replaced by prosthetic components made of metal alloys, high-grade plastics and polymeric materials. Much of the other anatomical structure of the knee, such as the connecting ligaments, remain intact.

The human knee is a very complex joint because the surfaces must roll and glide properly as the knee alternates from flexion to extension. Prostheses attempt to conform to the complexity of the joint, and attempt to replicate the more complicated motions and to take advantage of the posterior cruciate ligament (PCL) and collateral ligaments for support.

Up to three bone surfaces may be replaced during a total knee arthroplasty: the distal portion of the femur, encompassing the medial and lateral condyles, the proximal portion of the tibia, and occasionally, the posterior surface of the patella. Components are usually designed so that metal articulates against plastic, which provides smooth movement and results in minimal wear.

The metal femoral component curves around the distal end of the femur and has an anterior indentation so the patella can articulate smoothly as the knee alternates between flexion and extension. Usually, one large femoral component is applied the distal end of the femur. If only one condylar portion of the femur is damaged, a smaller component may be used. This is referred to as a unicompartmental knee replacement. Some designs such as posterior stabilized designs, have an internal structure that cooperates with corresponding structure on a tibial component to help prevent the femur from sliding anteriorly too far on the tibia when the knee is placed in flexion. The tibial component is typically a generally flat metal platform with a polyethylene bearing. The bearing may be part of the platform or separate with either a flat surface or a raised, sloping surface. The patellar component is typically a dome-shaped piece of polyethylene that duplicates the shape of the patella anchored with bone cement.

In a conventional total knee arthroplasty procedure, a patient's knee is placed in flexion so that all surfaces to be replaced are patent and accessible to a surgical team. A standard surgical approach is through a sagittal incision on an anterior surface of the knee slightly medial to the patella, although some surgeons will approach the joint from an incision lateral and superior to the patella. The incision through the skin is usually 6" to 12" in length. The large quadriceps muscle and the patella are moved to the side to expose the bone surfaces of the knee.

After taking several measurements to ensure that a new prosthetic component will fit properly, the surgeon begins to resect portions of the distal femur and/or proximal tibia. Depending on the type of implant used, the surgeon may begin with either the femur or the tibia. Special instrumentation such as cutting blocks can be used to ensure accurate resection of the damaged surfaces at the distal portion of the femur. The devices help shape the distal end of the femur so it conforms to the inside surface of the new prosthesis. If it is necessary to remove portions of the condyle or other distal portions of the femur, the surgeon typically uses instrumentation which is connected to the femur in order to resect the necessary portions of the femur so that the implant can be properly positioned or oriented. In some cases however, such as a revision case, the distal portion of the femur is so severely deteriorated that it requires augmentation before the implant can be installed.

The tibia is then modified by making a transverse cut across the bone and a central portion of the tibia is prepared. The surgeon removes just enough of the tibia so that when the prosthesis is inserted, it recreates the joint line at the same level as prior to surgery. If any ligaments around the knee have contracted due to degenerative disease or injury before the surgery, the surgeon carefully releases them so that they function as close to the normal state as possible.

During the total knee arthroplasty, proper positioning of the superior/inferior joint line between the femoral component and tibial component is critical to a successful operation. Joint line malpositioning can adversely affect the patellafemoral mechanics and may lead to anterior knee pain and may reduce range of motion. Proper superior/inferior joint line positioning is equally critical in a revision total knee arthroplasty. During a revision total knee arthroplasty however, determining the superior/inferior joint line position is particularly difficult because there is often significant deterioration of the proximal fibia and distal femur and, therefore, an absence of adequate anatomical landmarks for an accurate joint line positioning. To aid in the determination of the proper superior/inferior position of the joint line between the femoral component and tibial component, a trial femoral component is often used. During the replacement procedure, testing of proper positioning for the prosthetic components can be conducted with the trial components in place without exposing the actual components to potential wear or degradation.

Existing methods of determining proper superior/inferior joint line positioning include ratios that are determined based upon the position of the tibial plateau relative to the length of the patella tendon. Ratios dependent on the tibial plateau position may be faulty because they must assume the correct level of the tibial plateau which may not be achieved. Ratios dependent on the length of the patella tendon can be time-consuming, confusing and do not have a relationship to the total knee arthroplasty instrumentation. A need exists, therefore, for a joint line positioning apparatus that will help determine the proper superior/inferior joint line position between the femoral component and the tibial component during a total knee arthroplasty or a revision total knee arthroplasty when existing anatomical landmarks or portions of the femur are damaged or nonexistent.

SUMMARY

The present invention is applicable to knee repair, reconstruction, and replacement surgery and specifically to total knee arthroplasty and revision total knee arthroplasty procedures. Methods and devices according to certain embodiments of the present invention facilitate the proper positioning of the superior/inferior joint line between the femoral component and the tibial component during a revision total knee arthroplasty procedure.

During a revision total knee arthroplasty procedure, the surgeon must remove the previously implanted femoral component. Often there is significant deterioration of the proximal fibia and the distal femur and a loss of adequate anatomical landmarks for accurate joint line positioning. Methods and devices according to one embodiment of the present invention provide a femoral trial with a mark indicating a proper joint line position. According to some embodiments, a surgeon can then use the mark to assist in determining the proper superior-inferior joint line position between the femoral component and the tibial component.

According to one embodiment, a method comprises providing a femoral trial component, the femoral trial component comprising an anterior flange and at least one mark on the anterior flange of the femoral trial component to indicate a desired patellofemoral contact point in extension; referencing the mark on the femoral trial component during a surgical procedure to assist in determining a proper superior-inferior joint line position between a tibial prosthetic component and a femoral prosthetic component; installing the femoral prosthetic component based at least in part on the determination of the proper superior-inferior joint line position between the tibial component and the femoral component; installing the tibial prosthetic component based at least in part on the determination of the proper superior-inferior joint line position; and completing the surgical procedure with the femoral component and tibial component in proper position.

According to another embodiment, the surgical procedure can be a revision total knee arthroplasty. According to another embodiment, the surgical procedure can be a primary total knee arthroplasty. According to yet another embodiment, the femoral trial component can further comprise additional marks indicating a distance from the mark on the femoral trial indicating the proper patellofemoral contact point in extension. According to yet another embodiment, one of the additional marks can be referenced during a surgical procedure. According to another embodiment, the additional marks can be referenced during a surgical procedure to determine a position of an item relative to the desired position based at least in part on observing with which of the additional marks the item is aligned.

According to yet another embodiment, a method for determining proper superior-inferior joint line positioning can further comprise mating reference instrumentation to an anatomical landmark. According to still yet another embodiment, the anatomical landmark can be a femur. According to still yet another embodiment, determining the proper superior-inferior joint line positioning can further comprise marking a medial or a lateral side of a femur to further indicate the proper superior-inferior joint line between the tibial and femoral components.

According to another embodiment of the present invention, a surgical component system comprises at least one femoral prosthetic component, at least one tibial prosthetic component, a trial femoral component, the trial femoral component comprising at least one mark on an anterior flange, the mark adapted to be compared to the position of a patellar component to assist in determining a proper superior-inferior joint line between the femoral component and the tibial component in extension. According to yet another embodiment, the surgical system can be adapted for use in a revision total knee arthroplasty procedure or a primary total knee arthroplasty procedure. According to still yet another embodiment, the femoral trial component can further comprise additional marks to indicate a distance from the mark on the femoral trial indicating the proper patellofemoral contact point in extension. According to still yet another embodiment, distance indicators can be associated with the additional marks indicating a distance proximal or distal to the proper superior-inferior joint line position. According to other embodiments, at least one of the additional marks can be adapted to be referenced to determine a position of an item relative to the proper superior-inferior joint line position based at least in part on observing with which of the additional marks the item is aligned. According to another embodiment, reference instrumentation can be adapted to be mated to an anatomical landmark. According to yet another embodiment, the anatomical landmark can comprise a femur. According to another embodiment, the surgical system can further comprise instrumentation adapted to mark a medial or lateral side of a femur to further indicate the proper superior-inferior joint line between the tibial and femoral components.

According to still yet another embodiment, a method for determining proper superior-inferior joint line positioning between a femoral component and a tibial comprises removing a previously implanted femoral component, placing a trial femoral component, the trial femoral component comprising at least one mark on an anterior flange to indicate a proper superior-inferior joint line position and extension, placing a leg in full extension, determining whether a patellar component is superior to, inferior to, or aligned with the at least one mark, resecting a distal portion of a femur if the patellar component is superior to the at least one mark, distalizing the distal portion of the femur through the use of femoral augments if the patellar component is inferior to the at least one mark, removing the trial femoral component, placing a femoral prosthetic component, and placing a tibial prosthetic component.

DETAILED DESCRIPTION

Methods and devices according to certain embodiments of the present invention assist a surgeon to determine a proper superior/inferior position of the tibiofemoral joint line of the femoral component during a revision total knee arthroplasty. The present invention can be equally useful in a primary total knee arthroplasty, but by way of example, the present invention will be described in the context of a revision total knee arthroplasty.

Figure 1:
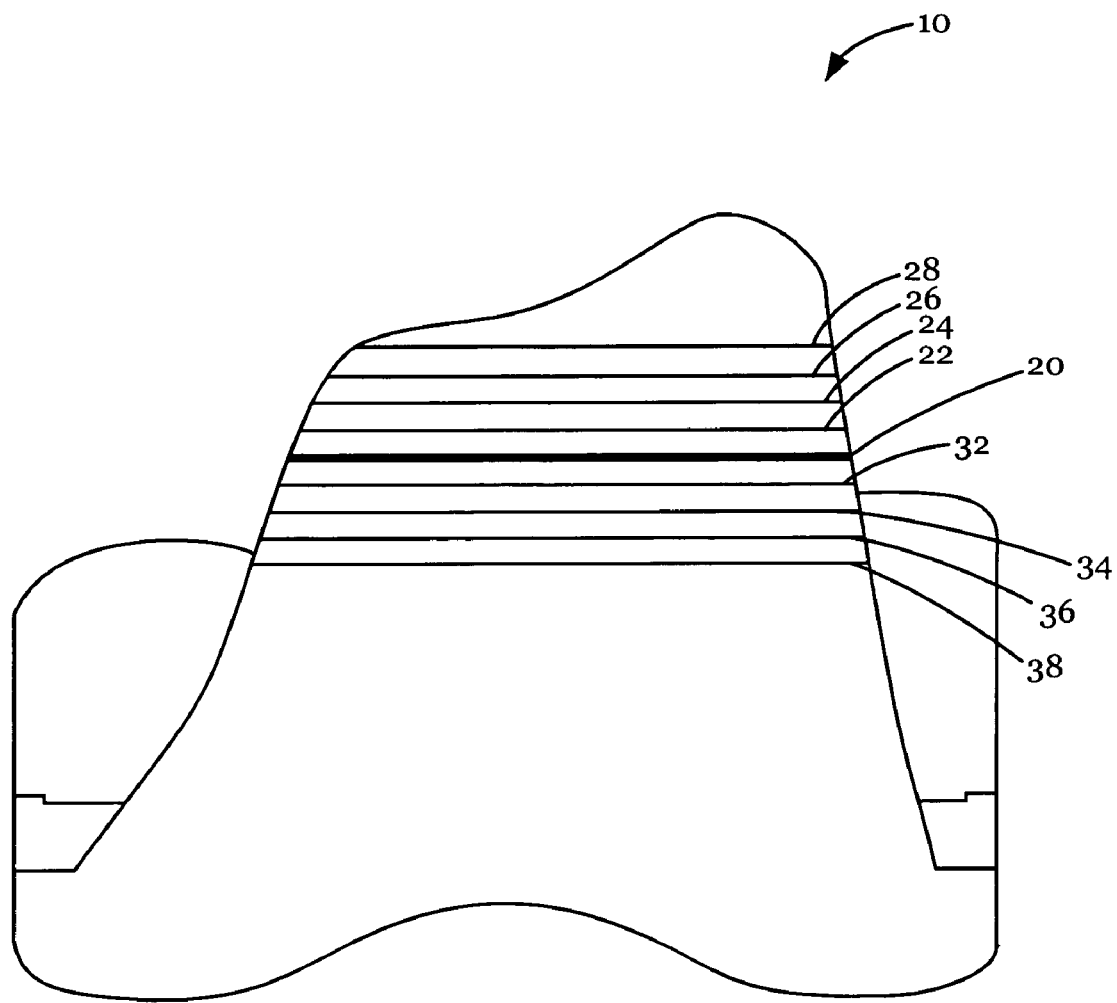
FIG. 1 is an illustration of a trial prosthetic component to assist in proper positioning of the superior-inferior joint line between the femoral and tibial components according to one embodiment of the present invention.

Referring now to FIG. 1, FIG. 1 shows one embodiment of the present invention comprising a femoral trial 10. The femoral trial 10 comprises a mark 20 indicating a desired point on the femoral trial 10. According to some embodiments, the desired point can be a proper patellofemoral contact position in extension. In other embodiments, the desired point could be other joint-line indicating features such as ligament or bone landmarks or intermediate positioning features such as a bone spike alignment. In other embodiments, the mark 20 could indicate a range of proper patellofemoral contact positions. According to the embodiment depicted, the mark is a transverse laser etch line on an anterior flange of the femoral trial 10. In other embodiments, the mark could be a mechanically etched line, an imprint from a mold, a drawn or painted line, or any other mark.

The femoral trial 10 further comprises a plurality of additional marks 22-38 indicating a distance from the mark 20. According to the embodiment depicted, the plurality of additional marks 22-38 are equally spaced. In the embodiment depicted, the additional marks 22-28 are located proximally to the mark 20 and the additional marks 32-38 are located distally to the mark 20. According to some embodiments, the additional marks 22-38 further comprise a plurality or numbers designating a distance proximal or distal from the mark 20.

Figure 2:
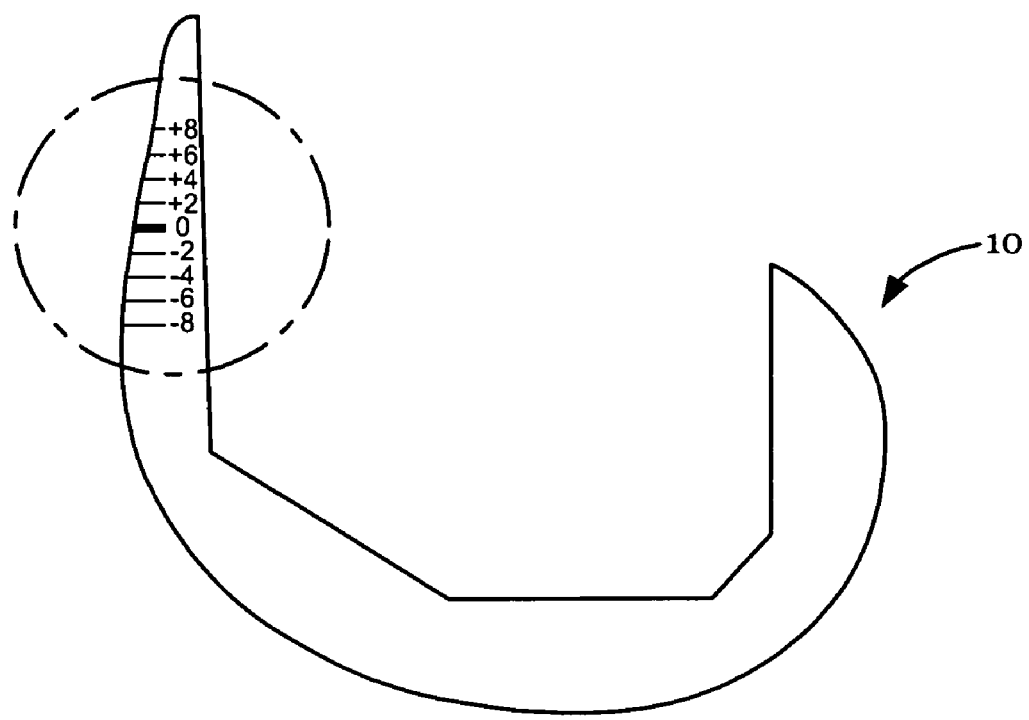
FIG. 2 is a lateral view of the trial prosthetic component illustrated in FIG. 1 depicting some of the unique features of the prosthetic component according to one embodiment of the present invention.
Figure 3:
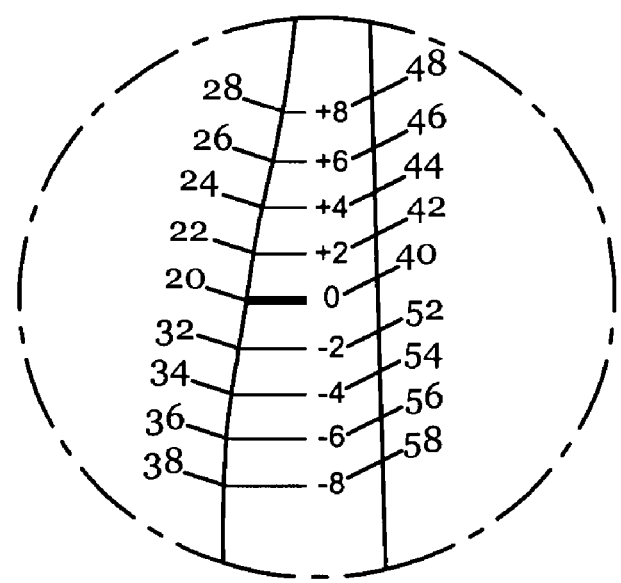
FIG. 3 is a more detailed view of a portion of the trial prosthetic component illustrated in FIG. 2 depicting some of the unique features and aspects of the trial prosthetic component according to one embodiment of the present invention.

Referring now to FIGS. 2 and 3, FIG. 2 illustrates a lateral view of the femoral trial of FIG. 1. FIG. 3 illustrates a close up of a portion of FIG. 2. According to the embodiment depicted, the anterior flange of the femoral component 10 has a lateral side. The lateral side of the anterior flange comprises extensions of the additional marks 20-38 shown in FIG. 1. The lateral edge of the anterior flange depicted in FIG. 3 further comprises a plurality of numbers 40-58 indicating a distance from a corresponding additional mark to the mark 20. For example, the additional mark 22 in the embodiment shown is two millimeters proximal to the mark 20. The number 42 corresponding to the additional mark 20 thus indicates "+2." Similarly, the additional mark 32 is two millimeters distal to the mark 20, thus the number 52 corresponding to the additional mark 32 indicates "−2." In the embodiment depicted, negative numbers indicate distance in millimeters distal to the mark 20, and positive numbers indicate a distance in millimeters proximal to the mark 20. In other embodiments, other units or spacings can be used.

Figure 4:
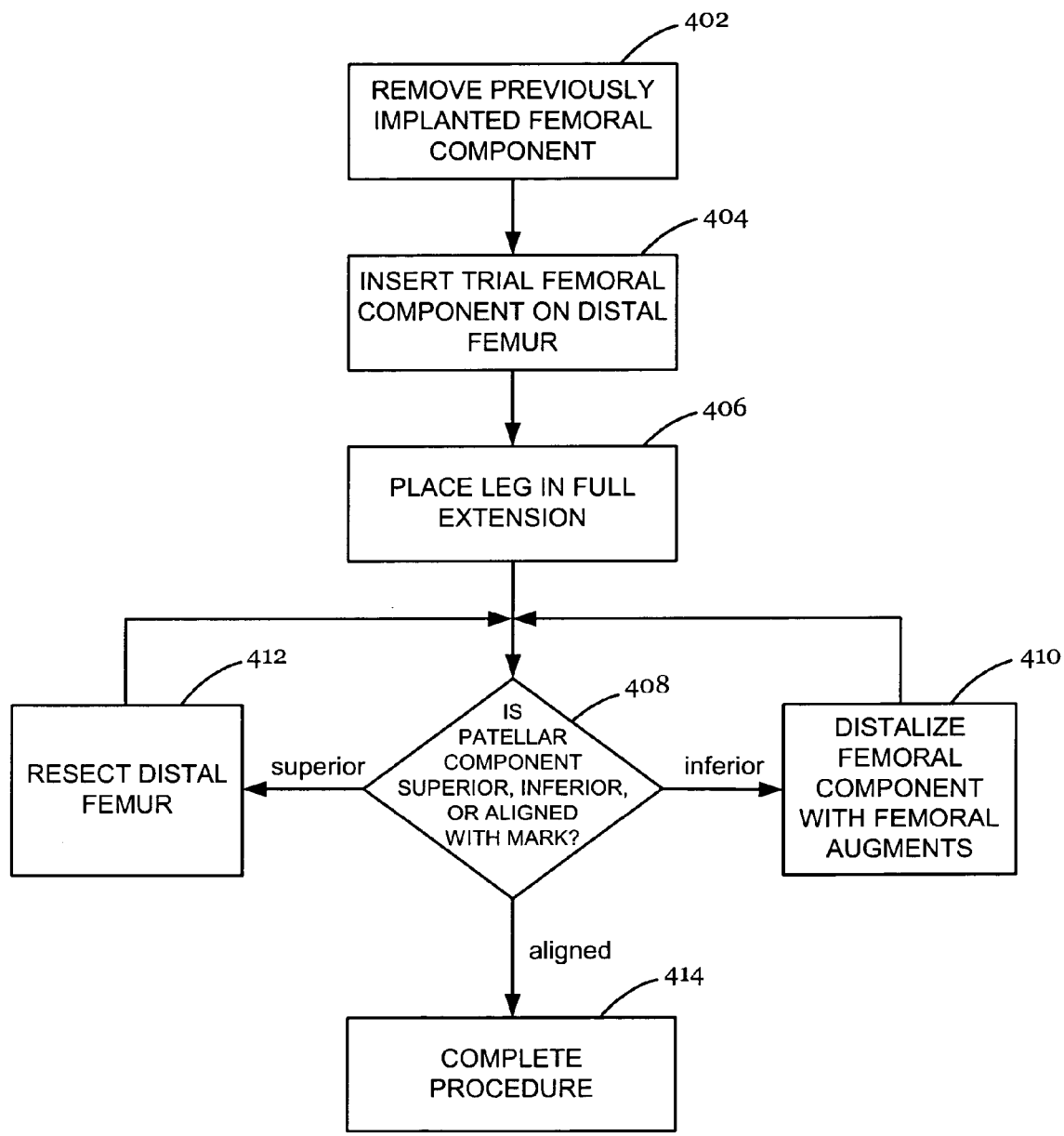
FIG. 4 shows a method for determining the proper superior-inferior joint line between the femoral and tibial components during a total knee orthroplasty procedure and for properly installing the femoral and tibial components according to the proper superior-inferior joint line position in accordance with one embodiment of the present invention.

FIG. 4 illustrates a method in accordance with the present invention. Although the method shown in FIG. 4 could be carried out with other devices or other embodiments of the present invention, it will be described using the embodiments depicted in FIGS. 1-3. FIG. 4 illustrates a method in accordance with certain embodiments of the present invention for placing a femoral component using a femoral trial 10 comprising a mark indicating a desired patellofemoral contact point in extension during a surgical procedure. The method illustrated in FIG. 4 begins in block 402 wherein a previously implanted femoral component is removed. Following removal of the previously implanted tibial and femoral components, there is often significant bone deterioration on the proximal tibia and the distal femur and an absence of adequate anatomical landmarks to indicate accurate joint line positioning. Once the previously implanted femoral component is removed, the distal femur is prepared with the standard revision technique and the method illustrated in FIG. 4 proceeds to block 404, wherein the trial femoral component 10 is inserted onto the distal femur. Inserting the trial femoral component 10 onto the distal femur allows the surgeon to assess positioning and alignment of the femoral trial prior to placing a new femoral component. According to one embodiment, the trial femoral component 10 can comprise a mark 20 indicating a proper patellofemoral contact point in extension. According to one embodiment, the trial 10 can further comprise a plurality of marks 28-38 as illustrated in FIG. 1. According to certain embodiments, the marks can extend to a lateral or medial side of the femoral trial 10 as illustrated in FIGS. 2 and 3. According to one embodiment, the femoral trial 10 can further comprise numbers 48-58 indicating a distance proximal to or distal to the mark 20 indicating the proper patellofemoral contact point in extension.

Once the trial femoral component 10 is inserted onto the distal femur, the method illustrated in FIG. 4 proceeds to block 406 wherein the patient's leg is placed in full extension. When the patient's leg is placed in full extension, the patellar component is brought in place above the femoral trial component 10. Once the patellar component is in place above the femoral trial component, the method proceeds to block 408 wherein it is determined whether the patella component is superior to, inferior to, or aligned with the mark 20 indicating the desired patellafemoral contact position on the femoral trial component. If the patellar component is superior to the mark 20 on the femoral trial 10 indicating the desired patellofemoral contact point in extension, the method illustrated in FIG. 4 proceeds to block 412 wherein the distal femur can be resected in order to proximalize the distal femur component and to bring the patellar component into proper alignment with the desired patellafemoral contact position. According to one embodiment, a surgeon or other member of a surgical team can examine the marks 22-28 and corresponding numbers 42-48 to assist in determining how much the resection should occur on the distal femur. For example, the surgeon can determine that the patellar component aligns with mark 24 on the femoral trial 10. Mark 24 on the femoral trial 10 corresponds to number 42 which, according to the embodiment depicted in FIG. 3, can indicate to the surgeon that the patellar component is four millimeters superior to the desired patellofemoral contact point 20. Thus, in this example, the surgeon can determine that the distal femur should be resected sufficient to proximalize the trial femoral component 10 a total of four millimeters.

If it is determined in block 408 that the patellar component is inferior to the mark 20 indicating the desired patellofemoral contact point, the femoral component 10 can be distalized through the use of femoral augments. Distalizing the femoral trial 10 through the use of femoral augments can function to bring the patellar component into proper alignment with the desired joint line position between the femoral and tibial prosthetic components as indicated by the mark 20 on the femoral trial 10. According to one embodiment, the surgeon or other member of the surgical team can compare a position of the patellar component with the marks 32-38 and corresponding numbers 52-58 to assist in determining the degree to which the femoral trial 10 should be distalized through the use of femoral augments. For example, the surgeon can determine that the patellar component aligns with mark 34 on the femoral trial 10. Mark 34 on the femoral trial 10 corresponds to number 54, which can indicate, according to the example illustrated in FIG. 3, that the patellar component is four millimeters distal to the desired patellofemoral contact point as indicated by the mark 20 on the femoral trial 10. Thus, according to this example, the surgeon could use sufficient femoral augments to distalize the femoral trial 10 a total of four millimeters in order to establish the correct joint line between the femoral and tibial prosthetic components.

Following block 412 or 410, the example method illustrated in FIG. 4 returns to block 408 wherein it is again determined whether the patellar component is superior to, inferior to, or aligned with the mark. If it is determined in block 408 that the patella component is aligned with the mark indicating the desired point on the femoral trial component, the method proceeds to block 414 wherein the procedure is completed according to standard surgical technique. Completing the procedure according to standard surgical technique includes, for example, placing the femoral prosthetic component in proper position as determined by the method described above to achieve the desired joint line between the femoral and tibial prosthetic components. Completing the procedure according to standard surgical technique can further comprise placing the tibial prosthetic components in proper position as determined by the method described above which will achieve the desired joint line between the femoral and tibial prosthetic components.

According to other embodiments, the proper patellofemoral contact position can be further identified by mating reference instrumentation to existing anatomical landmarks, implanted components, or to other femoral or tibial bone reactions. According to other embodiments, the proper patellofemoral contact position can be further identified by marking a medial and/or lateral sides of the femur at the patellofemoral contact point when the leg is paced in extension prior to removal of the primary components. Following the removal of the primary components, a reference plate can be attached to a revision femoral cutting block. The reference plate can then be compared to the mark on the medial and/or lateral sides of the femur to further assist in initial femoral resection alignment.

The foregoing description of embodiments of the invention has been presented only for the purpose of illustration and description and is not intended to be exhaustive or to limit the invention to the precise forms disclosed. Numerous modifications and adaptations thereof will be apparent to those skilled in the art without departing from the spirit and scope of the present invention.

What is claimed is:

1. A method for determining proper superior-inferior joint line positioning between a femoral component and a patellar component comprising:
   determining a primary superior-inferior joint line between a tibial component and a femoral component;
   providing a femoral trial component, the femoral trial component comprising an anterior surface, and a distal surface, the anterior and distal surfaces determined when a patient's leg is in extension and the femoral trial component is placed on a distal portion of the femur such that the anterior surface is adjacent to a patellar component and the distal surface is aligned with a lateral and medial condyle articular surface of a femur, and at least one mark on the anterior surface of the femoral trial component to indicate a desired patellofemoral contact point in extension;
   placing the patellar component above the femoral trial component;
   referencing the mark on the femoral trial component during a surgical procedure to assist in determining a secondary superior-inferior joint line position between a patellar component and a femoral prosthetic component, wherein determining the secondary superior-inferior joint line position includes using the at least one mark on the anterior surface of the femoral trial component to indicate a desired patellofemoral contact point in extension by determining whether the patellar component is superior, inferior, or aligned with the at least one mark of the anterior surface of the femoral trial component and either proximalizing the femoral component if the patellar component is superior to the at least one mark, distalizing the femoral component if the patellar component is inferior to the at least one mark, or maintaining the position of the femoral component if the patellar component is aligned with the at least one mark;
   installing the femoral prosthetic component based at least in part on the determination of the primary superior-inferior joint line position between the tibial component and the femoral component and the determination of the secondary superior-inferior joint line position between the patellar component and the femoral component and;
   completing the surgical procedure with the femoral component in proper position.

2. The method of claim 1, wherein the surgical procedure is a revision total knee arthroplasty.

3. The method of claim 1, wherein the surgical procedure is a primary total knee arthroplasty.

4. The method of claim 1, wherein the femoral trial component further comprises additional marks indicating a distance from the mark on the femoral trial indicating a proper patellofemoral contact point in extension.

5. The method of claim 4, further comprising referencing at least one of the additional marks during a surgical procedure.

6. The method of claim 5, wherein at least one of the additional marks is referenced to determine a position of an item relative to the desired position based at least in part on observing with which of the additional marks the item is aligned.

7. The method of claim 4, further comprising distance indicators associated with the additional marks indicating a specific numeric distance proximal or distal to the proper superior-inferior joint line position.

8. The method of claim 1, further comprising mating reference instrumentation to an anatomical landmark.

9. The method of claim 8, wherein the anatomical landmark is a femur.

10. The method of claim 1, further comprising marking a medial or lateral side of a femur to further indicate the proper superior-inferior joint line between the tibial and femoral components.

11. The method of claim 1 wherein the at least one mark on the anterior surface is on a lateral portion of the anterior surface.

12. The method of claim 1, wherein the patellar component is a prosthetic component.

* * * * *